United States Patent [19]

Gianturco

[11] Patent Number: 5,282,824
[45] Date of Patent: Feb. 1, 1994

[54] PERCUTANEOUS STENT ASSEMBLY

[75] Inventor: Cesare Gianturco, Champaign, Ill.

[73] Assignee: Cook, Incorporated, Bloomington, Ind.

[21] Appl. No.: 899,109

[22] Filed: Jun. 15, 1992

Related U.S. Application Data

[63] Continuation of Ser. No. 594,050, Oct. 9, 1990, abandoned.

[51] Int. Cl.$^5$ .................... A61M 29/00; A61F 2/06
[52] U.S. Cl. .................... 606/198; 606/191; 623/1
[58] Field of Search .............. 606/108, 153, 191, 195, 606/198, 200; 623/1, 11, 12

[56] References Cited

U.S. PATENT DOCUMENTS

| | | | |
|---|---|---|---|
| 3,657,744 | 4/1972 | Ersek | 606/153 |
| 4,512,338 | 4/1985 | Balko et al. | 606/191 |
| 4,580,568 | 4/1986 | Gianturco . | |
| 4,776,337 | 10/1988 | Palmaz | 623/1 |
| 4,830,003 | 5/1989 | Wolff et al. | 606/191 |
| 5,035,706 | 7/1991 | Gianturco et al. | 606/198 |
| 5,104,404 | 4/1992 | Wolff | 623/1 |

OTHER PUBLICATIONS

David Mirich et al., "Percutaneously Placed Endovascular Grafts for Aortic Aneurysms: Feasibility Study," *Radiology* 1989; 170:1033-1037.

*Primary Examiner*—Stephen C. Pellegrino
*Assistant Examiner*—William Lewis
*Attorney, Agent, or Firm*—Woodard, Emhardt, Naughton, Moriarty & McNett

[57] ABSTRACT

A self-expanding stent assembly consisting of one or more Z-stents connected to one another and covered by a flexible sleeve, which can be made from either nylon, plastic or another suitable material. The stents are formed of stainless steel wire arranged in a closed zigzag configuration which includes an endless series of struts that are joined by an equal number of joints. The stent assembly is compressible into a reduced diameter size for insertion into, and possible removal from, a body passageway. After being properly positioned within a body passageway, the stent assembly is allowed to expand to its larger diameter shape, wherein the sleeve is pressed against the walls of the passageway by the stents. One application of the invention includes dilating a biliary duct which has been occluded by a tumorous growth. The advantage being that the sleeve prevents the tumor from growing between the gaps created by the stent which would otherwise restenose the passageway. Another intended application is to repair aneurysms. In this configuration, the stents are postioned on either side of an aneurysm, and the sleeve forms and artificial arterial wall which spans the aneurysm.

6 Claims, 4 Drawing Sheets

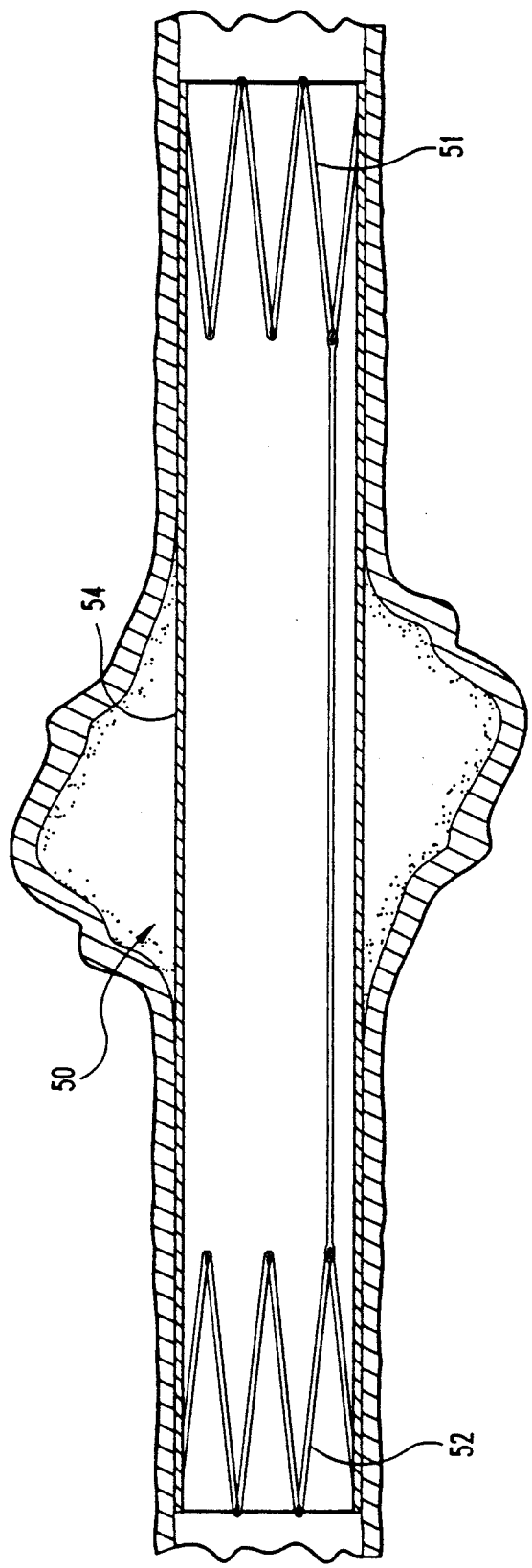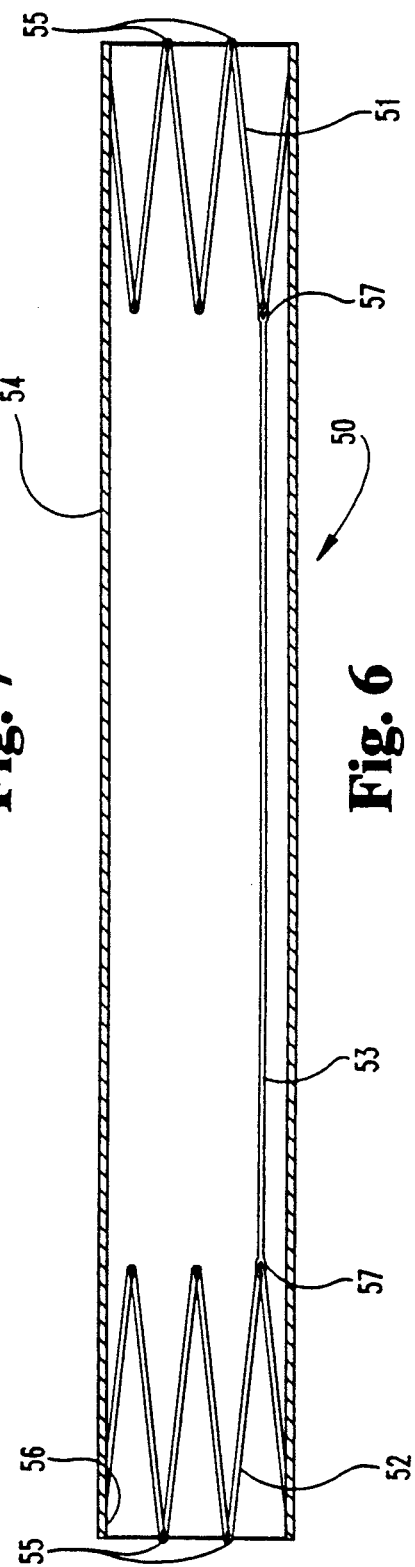
Fig. 7
Fig. 6

PERCUTANEOUS STENT ASSEMBLY

This application is a continuation of application Ser. No. 07/594,050, filed Oct. 9, 1990, now abandoned.

BACKGROUND OF THE INVENTION

1. Field of the Invention

This invention relates generally to vascular stents for use in preventing restenosis of passageways and ducts in the body and to repair aneurysms percutaneously.

2. Description of the Prior Art

It is desirable that means be provided which will prevent the restenosis of a passage or duct due to the invasion of tissue between the wire struts of the stent. Such a situation often occurs where a tumor has invaded a biliary tract. In those cases, a wire stent tends to provide only temporary relief from occlusion because the tumor often tends to grow between the wire struts, eventually resulting in a restenosed passageway. Gianturco U.S. Pat. No. 4,580,568 exemplifies such conventional wire stents. While Gianturco '568 discloses a wire stent to reduce flow defects in arteries, ducts and the like within the body, it does not solve the problem of tissue growth between the wire struts of the stent. Thus, conventional wire stents do not necessarily provide an acceptable long-term solution in the face of malignant tissue growth, nor do such stents provide a means to repair aneurysms percutaneously.

Reference is also made to U.S. patent application Ser. No. 422,606, also by Gianturco. That application teaches a stent structure and method which permits a stent to be easily retrieved from the body percutaneously, some time after being successfully implanted. In many instances, such an advantage would be suitable to the present invention.

There remains a need for a percutaneous stent assembly that is self-expanding, yet is capable of preventing or reducing restenosis. There is also need for a percutaneous stent assembly which is capable of repairing aneurysms.

SUMMARY OF THE INVENTION

One embodiment of the stent assembly of the present invention might include a flexible sleeve which is open at both ends. Attached to the flexible sleeve are one or more resiliently compressible stents. Each stent includes a plurality of struts which define a series of gaps therebetween. The stents are attached to the flexible sleeve such that the gaps defined by the stents are substantially covered by the sleeve. Because the sleeve is flexible, the percutaneous sleeved stent assembly is capable of elastically assuming a smaller first shape when compressed and and a larger second shape when allowed to expand. The smaller first shape allows the assembly to be passed percutaneously through a lumen into a passageway within the body. Upon implantation, the sleeved stent assembly is allowed to expand to assume the second larger shape wherein the flexible sleeve is pressed against the walls of the passageway by the stents to the maintain the passageway open.

One object of the present invention is to provide an improved percutaneous stent assembly.

Related objects and advantages of the present invention will be apparent from the following description.

BRIEF DESCRIPTION OF THE DRAWINGS

FIG. 6 is a sectioned side elevation of another preferred embodiment of the present invention.

FIG. 7 is a sectioned side elevation of the structure of FIG. 4 implanted to span an aneurysm in an artery.

DESCRIPTION OF THE PREFERRED EMBODIMENTS

Figure 1:
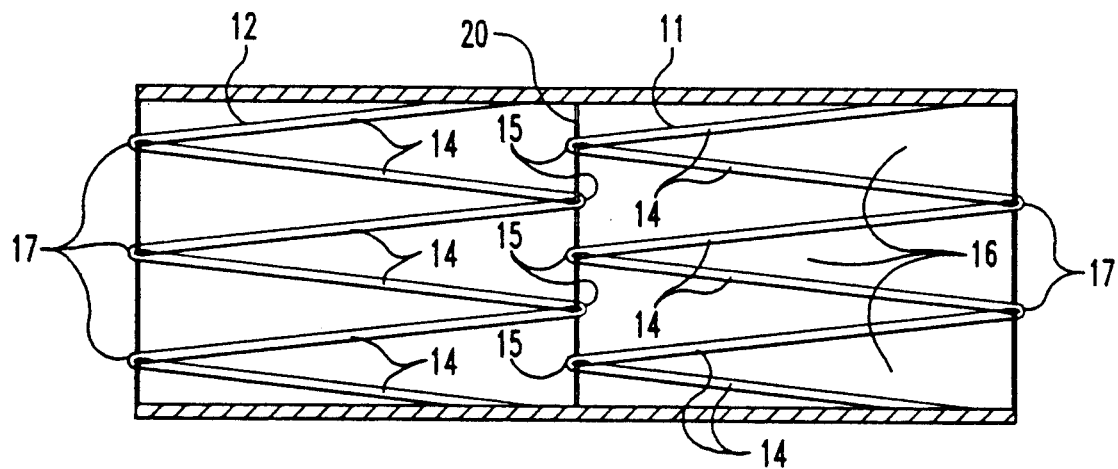
FIG. 1 is a sectioned side elevation of a preferred embodiment of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now more particularly to the drawings, there is illustrated in FIG. 1 a sectioned side elevation of a preferred embodiment of the percutaneous stent assembly 10 of the present invention which includes two stents, 11 and 12 respectively, surrounded by a flexible sleeve 13. Stents 11 and 12 are formed from a length of stainless steel wire formed in a closed zig-zag configuration. The ends of the wire can be closed in a variety of ways, including the use of a sleeve which is welded or tightly pinched against the ends of the wire to produce a continuous or endless configuration. Each stent 11 and 12 comprises a plurality of struts 14 connected to one another by a series of joints 15 and 17, which are better illustrated in FIG. 1A. In most respects, stents 11 and 12 are similar to the Z-stent described in U.S. Pat. No. 4,580,568 (Gianturco '568), which description is incorporated herein by reference. Each joint 15 and 17 defines an eye 18, which can be shaped by bending the wire to form a cusp and, then, welding or soldering the wire back upon itself. Each serial pair of struts 14 defines a gap 16 therebetween. The stents 11 and 12 are attached to sleeve 13, which in this case is nylon, by stitching or gluing the joints 17 at either end of the stent assembly to the sleeve 13. If the sleeve were made of plastic, the stents could be attached to the sleeve by embedding the stents in the plastic, it being understood that the means for attaching the stents to the sleeve can be varied depending on the sleeve material, and other factors, without diverging from the intended scope of the present invention.

Figure 1B:
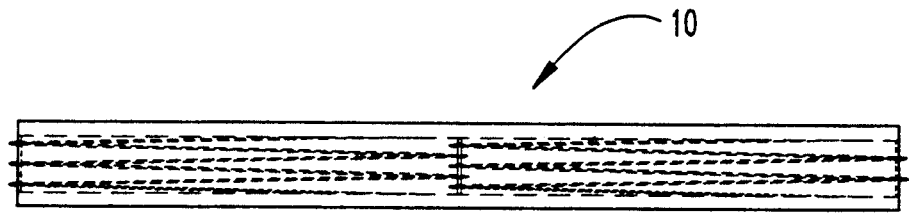
FIG. 1B is a side elevation of the embodiment shown in FIG. 1 in its compressed smaller shape for implantation in the body.
Figure 1A:
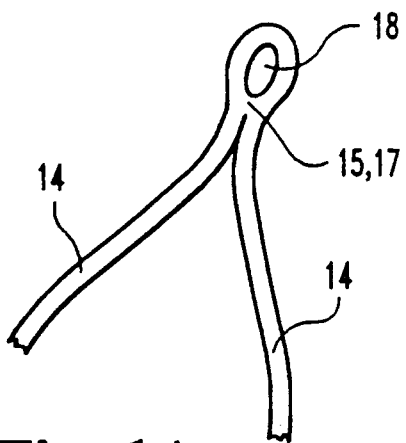
FIG. 1A is a detail of a junction between two struts of the stent portion of the embodiment shown in FIG. 1.
Figure 2:
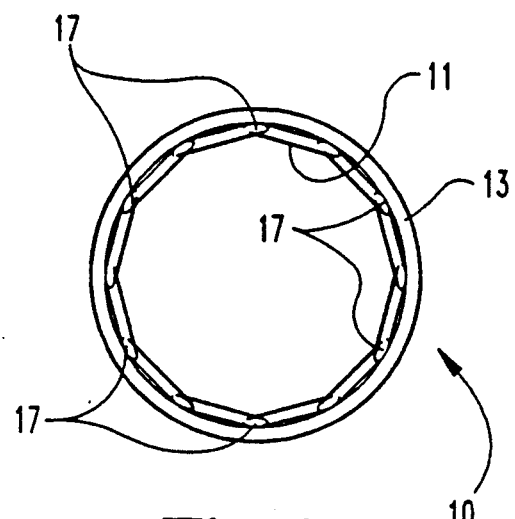
FIG. 2 is an end elevation of a preferred embodiment of the present invention.

The stent assembly resists contraction, or prevents overlapping of the stents 11 and 12, along the axis defined by sleeve 13 by serially tieing eyes 18 at joints 15 with thread 20. Thread 20 being preferably a monofiliment of bio-compatible material. The stent assembly must be able to resist contraction along its axis in order to be properly implanted and to avoid entangling the stents while in the compressed smaller shape. FIG. 1B shows a side elevation of percutaneous stent assembly 10 when compressed into its smaller first shape which facilitates implantation in the body. The same contraction resistant result can also be accomplished by directly connecting joints 15 through a variety of means, including welding, stiching or by utilizing interlocking eyes as disclosed in U.S. patent application Ser. No. 422,606.

Figure 3:
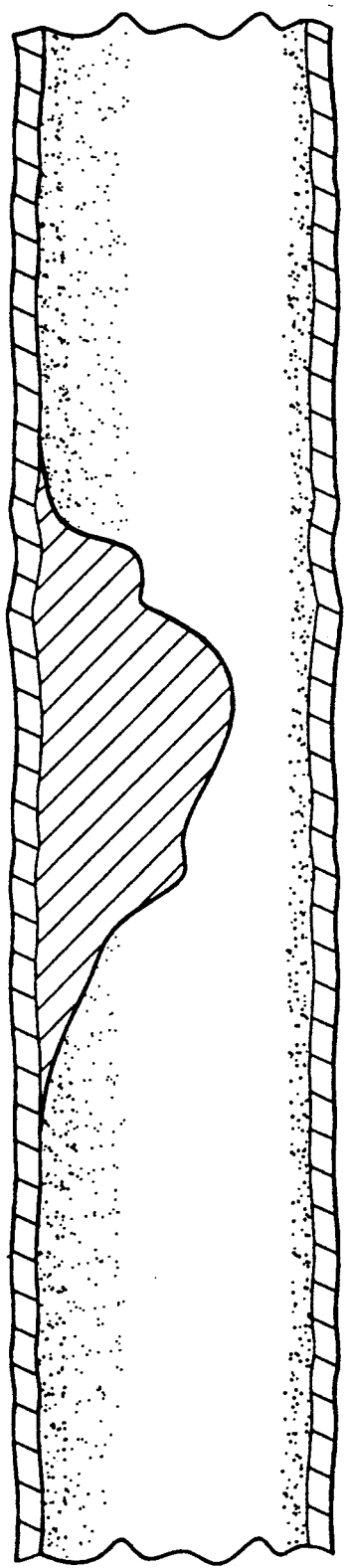
FIG. 3 is a section through a biliary duct showing a tumor growth which has partially occluded the duct.
Figure 4:
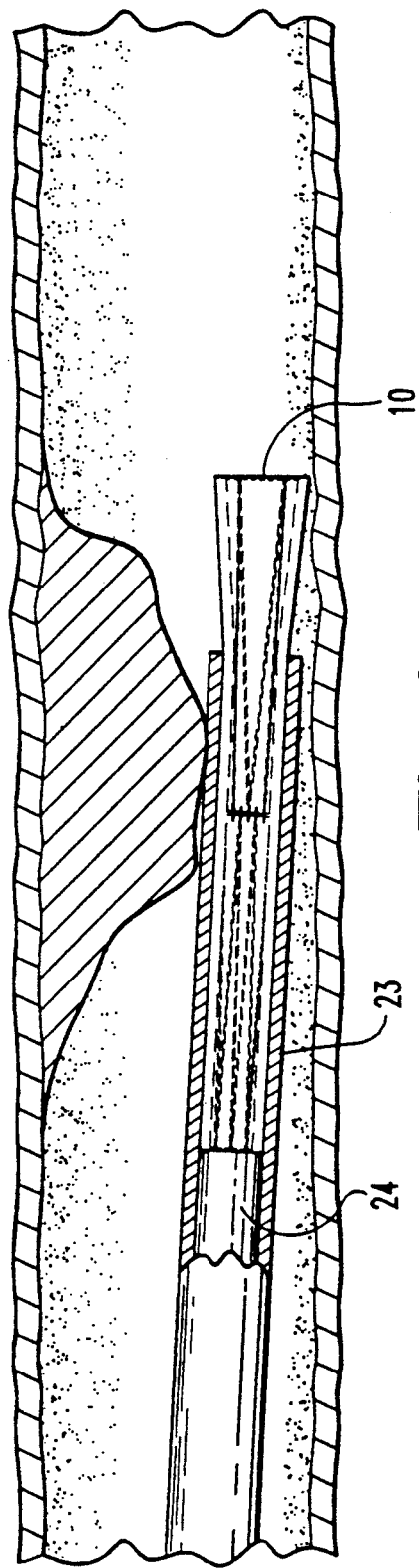
FIG. 4 shows the structure of FIGS. 1, 1B and 2 during implantation into the biliary duct of FIG. 3.
Figure 5:
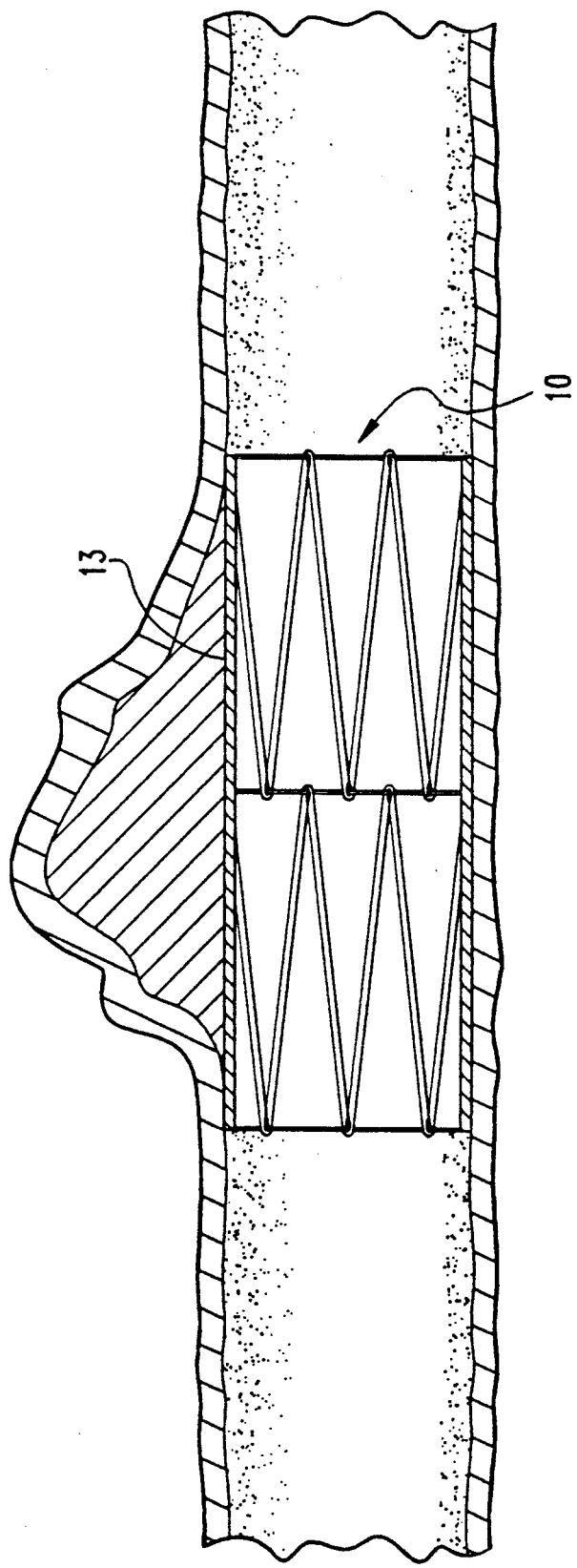
FIG. 5 is a sectioned side elevation of the structure of FIG. 1 implanted in a biliary duct adjacent to the tumor.

FIG. 3 shows a section of a biliary duct which is nearly occluded by the presence of a tumorous growth. While a conventional wire stent could be successfully implanted to redilate the opening in the duct, it would render only a temporary solution because the tumor would continue to grow between the struts of the stent, eventually resulting in a restenosed passageway in as little as a few weeks. The sleeve included in the present invention avoids this problem. FIG. 4 shows the compressed stent assembly 10 during implantation in the occluded duct of FIG. 3. As described in Gianturco '568 (col. 3, lines 5-18), the stent assembly 10 is pushed through a sheath 23 to the desired point in the body by flat-ended pusher 24, while in its compressed first shape. After arriving at the proper location, the sheath 23 is withdrawn, and the stent assembly 10 resiliently assumes its larger second shape, as illustrated in FIG. 5. The sleeve 13 prevents the tumor from growing between the struts of the stent, thus avoiding restenosis and affording a longer term solution than that possible with conventional wire stents.

Another preferred embodiment of the present invention, which is particularly suited for repairing aneurysms percutaneously, is illustrated in FIG. 6. The percutaneous stent assembly 50 includes resiliently expandable stents 51 and 52, rigid support rod 52 and nylon sleeve 54. Stents 51 and 52 are generally identical to stents 11 and 12 described earlier. The stents 51 and 52 are attached to sleeve 54 by stitching or gluing the joints 55, which are located at either end of the assembly, to the inner surface 56 of the sleeve.

During implantation, the rigid support rod 53 prevents the percutaneous stent assembly 50 from collapsing on itself along the axis defined by sleeve 54. This embodiment is implanted at the desired point in the body as described earlier for the previous embodiment. FIG. 7 shows stent assembly 50 after being implanted in an artery having an aneurysm. The stent assembly is secured in place when stents 51 and 52 press the sleeve 54 against the undamaged walls of the artery located on either side of the aneurysm. The sleeve 54 then forms an artificial arterial wall that spans the aneurysm. This removes pressure from the aneurysm, allowing it to heal.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A percutaneous stent assembly comprising:
   a flexible sleeve having an inner surface and an outer surface and being open at both ends;
   at least one resiliently compressible stent, each said stent including a plurality of struts defining a series of gaps between said struts;
   means for attaching said stents to said flexible sleeve such that said gaps defined by each said stent are substantially covered by said flexible sleeve;
   means for rendering said percutaneous stent assembly resistant to contraction along the axis defined by said flexible sleeve when the stent assembly is radially compressed into a smaller first shape and being axially pushed into position adjacent a stenosis in a passageway of a patient;
   wherein said percutaneous stent assembly defines said smaller first shape when radially compressed and resiliently defines a larger second shape when allowed to radially expand;
   said flexible sleeve is made of nylon; and
   said means for attaching said stents to said flexible sleeve consists of a plurality of stitches.

2. A percutaneous stent assembly comprising
   a flexible sleeve having an inner surface and an outer surface and being open at both ends;
   at least one resiliently compressible stent, each said stent including a plurality of struts defining a series of gaps between said struts;
   means for attaching aid stents to said flexible sleeve such that said gaps defined by each said stent are substantially covered by said flexible sleeve;
   means for rendering said percutaneous stent assembly resistant to contraction along the axis defined by said flexible sleeve when the stent assembly is radially compressed into a smaller first shape and being axially pushed into position adjacent a stenosis in a passageway of a patient;
   wherein said percutaneous stent assembly defines said smaller first shape when radially compressed and resiliently defines a larger second shape when allowed to radially expand;
   said stent comprising at least two resiliently compressible stents arranged end to end;
   said means for rendering the stent assembly resistant to contraction along the axis defined by said sleeve includes interconnecting adjacent ends of said at least two stents together;
   each said end of each said stent includes a plurality of eye portions; and
   said means for rendering the stent assembly resistant to contraction along the axis defined by said sleeve includes tieing at least one of said plurality of eye portions from each said stent to an adjacent said eye portion of an adjacent said stent.

3. The percutaneous stent assembly of claim 2 wherein said eye portions of each said stent are serially tied to said eye portions of an adjacent said stent.

4. A percutaneous stent assembly comprising:
   a resiliently compressible stent capable of being radially compressed into a smaller first shape but resiliently radially expanding into a larger second shape when allowed to expand, said stent having a plurality of interconnected struts which define a series of gaps therebetween when said stent is in said larger second shape;
   a flexible sleeve having an inner surface, an outer surface and being open at both ends; and means for attaching said stent to said flexible sleeve such that said gaps defined by each said stent are substantially covered by said flexible sleeve;

a second stent substantially identical to said first stent and being interconnected end-to-end with said first stent;

said flexible sleeve extends to cover said second stent; and said sleeve is formed from a flexible plastic material and said stents are embedded in said plastic.

5. The percutaneous stent assembly of claim 4 wherein said stents are tied end-to-end with a filament.

6. The percutaneous stent assembly of claim 5 wherein said sleeve is formed of nylon.

* * * * *